(12) United States Patent
Geiger et al.

(10) Patent No.: US 9,045,581 B2
(45) Date of Patent: Jun. 2, 2015

(54) POLYOLS DERIVED FROM A VEGETABLE OIL USING AN OXIDATION PROCESS

(75) Inventors: Eric J. Geiger, Brookings, SD (US); Nicole M. Becker, Huron, SD (US); Lawrence A. Armbruster, Bridgeville, PA (US)

(73) Assignee: Rhino Linings Corporation, San Diego, CA (US)

( * ) Notice: Subject to any disclaimer, the term of this patent is extended or adjusted under 35 U.S.C. 154(b) by 41 days.

(21) Appl. No.: 13/195,646

(22) Filed: Aug. 1, 2011

(65) Prior Publication Data

US 2011/0313074 A1  Dec. 22, 2011

Related U.S. Application Data

(62) Division of application No. 11/368,159, filed on Mar. 3, 2006, now Pat. No. 7,989,647.

(60) Provisional application No. 60/658,230, filed on Mar. 3, 2005.

(51) Int. Cl.
| | |
|---|---|
| *C08G 18/36* | (2006.01) |
| *C08G 18/42* | (2006.01) |
| *C08G 18/48* | (2006.01) |
| *C08G 18/64* | (2006.01) |
| *C08G 18/08* | (2006.01) |
| *C08G 18/40* | (2006.01) |
| *C07D 303/42* | (2006.01) |
| *C08G 18/66* | (2006.01) |
| *C11C 3/00* | (2006.01) |
| *C08G 101/00* | (2006.01) |

(52) U.S. Cl.
CPC ............... *C08G 18/36* (2013.01); *C08G 18/14* (2013.01); *C08G 18/4018* (2013.01); *C08G 18/4081* (2013.01); *C08G 18/64* (2013.01); *C07D 303/42* (2013.01); *C08G 18/0885* (2013.01); *C08G 18/4288* (2013.01); *C08G 18/6696* (2013.01); *C08G 2101/00* (2013.01); *C08G 2125/00* (2013.01); *C11C 3/006* (2013.01)

(58) Field of Classification Search
USPC ......... 521/111, 124, 128, 129, 130, 131, 170, 521/172, 173, 174, 176; 528/48, 52, 53, 54, 528/55, 56, 74.5, 76, 80, 85
IPC .............. C08G 18/36,18/0885, 18/14, 18/4018, C08G 18/4081, 18/4288, 18/64, 18/6696, C08G 2101/00, 2125/00; C11C 3/006
See application file for complete search history.

(56) References Cited

U.S. PATENT DOCUMENTS

| | | |
|---|---|---|
| 1,447,954 A | 3/1923 | Webster |
| 1,995,324 A | 3/1935 | Penniman |
| 2,167,266 A | 7/1939 | Kimball |
| 2,556,336 A | 6/1951 | Nye |
| 2,569,206 A | 9/1951 | Vogel |
| 2,606,890 A | 8/1952 | Polly et al. |
| 2,745,855 A | 5/1956 | Case |
| 2,787,601 A | 4/1957 | Detrick et al. |
| 2,833,730 A | 5/1958 | Barthel |
| 3,001,958 A | 9/1961 | Schwarcman |
| 3,396,473 A | 8/1968 | Turner |
| 3,535,156 A | 10/1970 | Turner |
| 3,576,929 A | 4/1971 | Turner et al. |
| 3,639,312 A | 2/1972 | Turner |
| 3,755,212 A | 8/1973 | Dunlap et al. |
| 3,778,205 A | 12/1973 | Turner et al. |
| 3,821,130 A | 6/1974 | Barron et al. |
| 3,846,478 A | 11/1974 | Cummins |
| 3,862,879 A | 1/1975 | Barron et al. |
| 3,963,699 A | 6/1976 | Rizzi et al. |
| 3,985,814 A | 10/1976 | Dougherty |
| 3,991,126 A | 11/1976 | Bacskai |
| 4,005,035 A | 1/1977 | Deaver |
| 4,022,941 A | 5/1977 | Prokai et al. |
| 4,045,498 A | 8/1977 | Deno |
| 4,076,679 A | 2/1978 | Turner |
| 4,116,987 A | 9/1978 | Deno |
| 4,171,395 A | 10/1979 | Tillotson |
| 4,185,146 A | 1/1980 | Burke |
| 4,229,362 A | 10/1980 | Norman |

(Continued)

FOREIGN PATENT DOCUMENTS

| | | |
|---|---|---|
| AU | 704532 | 3/1997 |
| DE | 3702615 | 1/1987 |
| DE | 4332292 | 9/1993 |
| DE | 19643816 | 10/1996 |
| JP | 62294538 | 12/1897 |
| JP | 5186556 | 7/1993 |
| WO | WO 97/07150 | 2/1997 |
| WO | WO 98/07777 | 2/1998 |
| WO | WO 99/12987 | 3/1999 |
| WO | WO 00/15684 | 3/2000 |

(Continued)

OTHER PUBLICATIONS

Silquest A-186 Silane and Silquest A-187 Silane; GE Advanced Materials—Silicones; 2004.*

(Continued)

*Primary Examiner* — Rabon Sergent
(74) *Attorney, Agent, or Firm* — Price Heneveld LLP

(57) ABSTRACT

A method for producing a vegetable oil-derived polyol having increased hydroxyl functionality by reacting a vegetable oil with an oxidizing agent in the presence of an organometallic catalyst is provided. The resulting higher functionality polyols derived from vegetable oil produced by the process are also provided. Also provided is a method for decreasing the acid value of a vegetable oil-derived polyol by reacting the vegetable oil-derived polyol with an epoxide component in the presence of a Lewis base catalyst. Urethane products produced using higher functional vegetable oil-derived polyols and/or lower acid vegetable oil-derived polyols are also provided.

16 Claims, No Drawings

(56) References Cited

U.S. PATENT DOCUMENTS

| | | | |
|---|---|---|---|
| 4,246,363 A | 1/1981 | Turner et al. | |
| 4,264,743 A | 4/1981 | Maruyama et al. | |
| 4,278,482 A | 7/1981 | Poteet et al. | |
| 4,286,003 A | 8/1981 | Higgins et al. | |
| 4,296,159 A | 10/1981 | Jenkines et al. | |
| 4,314,088 A | 2/1982 | Austin et al. | |
| 4,334,061 A | 6/1982 | Bossier, III | |
| 4,354,810 A | 10/1982 | Stidham | |
| 4,359,359 A | 11/1982 | Gerlach et al. | |
| 4,375,521 A | 3/1983 | Arnold | |
| 4,376,171 A | 3/1983 | Blount | |
| 4,390,739 A | 6/1983 | Michaelson et al. | |
| 4,393,253 A | 7/1983 | Michaelson et al. | |
| 4,405,393 A | 9/1983 | Tillotson | |
| 4,483,894 A | 11/1984 | Porter et al. | |
| 4,496,547 A | 1/1985 | Kawashima et al. | |
| 4,496,778 A | 1/1985 | Myers et al. | |
| 4,496,779 A | 1/1985 | Myers et al. | |
| 4,512,831 A | 4/1985 | Tillotson | |
| 4,515,646 A | 5/1985 | Walker et al. | |
| 4,518,772 A | 5/1985 | Volpenhein | |
| 4,530,941 A | 7/1985 | Turner et al. | |
| 4,535,110 A * | 8/1985 | Iseler et al. | 524/196 |
| 4,582,891 A | 4/1986 | Maki et al. | |
| 4,585,804 A | 4/1986 | Lancaster et al. | |
| 4,595,436 A | 6/1986 | Walker et al. | |
| 4,611,044 A | 9/1986 | Meyer et al. | |
| 4,642,320 A | 2/1987 | Turner et al. | |
| 4,657,790 A | 4/1987 | Wing et al. | |
| 4,686,242 A | 8/1987 | Turner et al. | |
| 4,687,788 A | 8/1987 | Hillshafer et al. | |
| 4,696,849 A | 9/1987 | Mobley et al. | |
| 4,701,475 A | 10/1987 | Turner | |
| 4,734,455 A | 3/1988 | Mobley et al. | |
| 4,740,367 A | 4/1988 | Force et al. | |
| 4,745,135 A | 5/1988 | Thomas et al. | |
| 4,745,136 A | 5/1988 | Thomas et al. | |
| 4,745,137 A | 5/1988 | Thomas et al. | |
| 4,798,849 A | 1/1989 | Thomas et al. | |
| 4,806,632 A | 2/1989 | McCoy et al. | |
| 4,825,004 A | 4/1989 | Rutzen et al. | |
| 4,843,138 A | 6/1989 | Tazewell et al. | |
| 4,853,054 A | 8/1989 | Turner et al. | |
| 4,853,280 A | 8/1989 | Poteet | |
| 4,861,803 A | 8/1989 | Turner | |
| 4,913,958 A | 4/1990 | Skaggs et al. | |
| 4,931,552 A | 6/1990 | Gibson et al. | |
| 4,942,278 A | 7/1990 | Sheinberg et al. | |
| 4,943,626 A | 7/1990 | McGrath et al. | |
| 4,952,687 A | 8/1990 | Bodor et al. | |
| 4,968,791 A | 11/1990 | Van Der Plank | |
| 4,973,681 A | 11/1990 | Watanabe | |
| 4,980,388 A | 12/1990 | Herrington et al. | |
| 5,010,117 A | 4/1991 | Herrington et al. | |
| 5,021,256 A | 6/1991 | Guffey et al. | |
| 5,032,622 A | 7/1991 | Herrington et al. | |
| 5,043,438 A | 8/1991 | Buter | |
| 5,071,975 A | 12/1991 | Ver Der Plank et al. | |
| 5,104,693 A | 4/1992 | Jenkines | |
| 5,104,910 A | 4/1992 | Turner et al. | |
| 5,106,874 A | 4/1992 | Porter et al. | |
| 5,106,884 A | 4/1992 | Turner et al. | |
| 5,106,967 A | 4/1992 | Mazur | |
| 5,126,494 A | 6/1992 | Gilheany et al. | |
| 5,194,281 A | 3/1993 | Johnston et al. | |
| 5,225,049 A | 7/1993 | Barmentlo et al. | |
| 5,231,199 A | 7/1993 | Willemse | |
| 5,274,145 A | 12/1993 | Gubelmann | |
| 5,324,846 A | 6/1994 | Hirshman et al. | |
| 5,397,810 A | 3/1995 | Ozaki et al. | |
| 5,440,027 A | 8/1995 | Hasenhuettl | |
| 5,447,963 A | 9/1995 | Pcolinsky et al. | |
| 5,482,980 A | 1/1996 | Pcolinsky | |
| 5,491,174 A | 2/1996 | Grier et al. | |
| 5,491,226 A | 2/1996 | Kenneally | |
| 5,496,869 A | 3/1996 | Williams et al. | |
| 5,504,202 A | 4/1996 | Hutchison | |
| 5,571,935 A | 11/1996 | Sekula et al. | |
| 5,576,027 A | 11/1996 | Friedman et al. | |
| 5,627,221 A | 5/1997 | Schumacher et al. | |
| 5,629,434 A | 5/1997 | Cusumano et al. | |
| 5,648,483 A | 7/1997 | Granberg et al. | |
| 5,681,948 A | 10/1997 | Miller et al. | |
| 5,688,860 A | 11/1997 | Croft | |
| 5,698,722 A | 12/1997 | Cusumano et al. | |
| 5,710,190 A | 1/1998 | Jane et al. | |
| 5,756,195 A | 5/1998 | Allen et al. | |
| 5,766,704 A | 6/1998 | Allen et al. | |
| 5,767,257 A | 6/1998 | Schafermeyer et al. | |
| 5,795,949 A | 8/1998 | Daute et al. | |
| 5,811,129 A | 9/1998 | Friedman et al. | |
| 5,869,546 A | 2/1999 | Gruss et al. | |
| 5,900,496 A | 5/1999 | Hou | |
| 5,902,854 A | 5/1999 | Kelley et al. | |
| 5,908,701 A | 6/1999 | Jennings et al. | |
| 5,922,779 A | 7/1999 | Hickey | |
| 5,945,529 A | 8/1999 | Corrigan et al. | |
| 6,015,440 A | 1/2000 | Noureddini | |
| 6,080,853 A | 6/2000 | Corrigan et al. | |
| 6,096,401 A | 8/2000 | Jenkines | |
| 6,100,394 A | 8/2000 | Collins et al. | |
| 6,107,433 A | 8/2000 | Petrovic et al. | |
| 6,121,398 A | 9/2000 | Wool et al. | |
| 6,133,329 A | 10/2000 | Shieh | |
| 6,174,501 B1 | 1/2001 | Noureddini | |
| 6,180,686 B1 | 1/2001 | Kurth | |
| 6,288,133 B1 | 9/2001 | Hagquist | |
| 6,388,002 B1 | 5/2002 | Baker et al. | |
| 6,420,446 B1 | 7/2002 | Chang | |
| 6,465,569 B1 | 10/2002 | Kurth | |
| 6,476,244 B2 | 11/2002 | Mahlum | |
| 6,562,901 B1 | 5/2003 | Asami et al. | |
| 6,624,244 B2 | 9/2003 | Kurth | |
| 6,649,667 B2 | 11/2003 | Clatty | |
| 6,686,435 B1 | 2/2004 | Petrovic et al. | |
| 6,759,542 B2 | 7/2004 | Mahlum | |
| 6,825,238 B2 | 11/2004 | Hohl et al. | |
| 6,864,296 B2 | 3/2005 | Kurth | |
| 6,867,239 B2 | 3/2005 | Kurth | |
| 6,881,763 B2 | 4/2005 | Kurth | |
| 7,989,647 B2 * | 8/2011 | Geiger et al. | 554/183 |
| 8,507,701 B2 * | 8/2013 | Yalamanchili et al. | 554/138 |
| 2002/0013396 A1 | 1/2002 | Benecke et al. | |
| 2002/0058774 A1 | 5/2002 | Kurth et al. | |
| 2002/0090488 A1 | 7/2002 | Kurth et al. | |
| 2002/0119321 A1 | 8/2002 | Kurth et al. | |
| 2002/0121328 A1 | 9/2002 | Kurth et al. | |
| 2002/0192456 A1 | 12/2002 | Mashburn et al. | |
| 2003/0039846 A1 * | 2/2003 | Roesler et al. | 428/447 |
| 2003/0105250 A1 | 6/2003 | Whiteker | |
| 2003/0143910 A1 | 7/2003 | Mashburn et al. | |
| 2003/0166735 A1 * | 9/2003 | Clatty | 521/155 |
| 2003/0191274 A1 | 10/2003 | Kurth et al. | |
| 2003/0220446 A1 | 11/2003 | Faler et al. | |
| 2004/0034163 A1 * | 2/2004 | Kurth | 524/589 |
| 2004/0209971 A1 | 10/2004 | Kurth et al. | |
| 2005/0131092 A1 | 6/2005 | Kurth et al. | |
| 2005/0131093 A1 | 6/2005 | Kurth et al. | |
| 2005/0182228 A1 | 8/2005 | Kurth et al. | |

FOREIGN PATENT DOCUMENTS

| | | |
|---|---|---|
| WO | WO 00/23491 | 4/2000 |
| WO | WO 01/04225 | 1/2001 |
| WO | WO 01/70842 | 9/2001 |

OTHER PUBLICATIONS

McGraw-Hill Publications, Modern Plastics Encyclopedia, vol. 45: No. 14A p. 100-01, 113, 352, 354, 356, 358-360, dated Oct. 1968.
Robert C. Weast, Ph. D., CRC Press, Cleveland, OH, Handbook of Chemistry and Physics, p. C-214-215, C-275, C-277, C-288-289, C-296-297, C-312-314, C-325-326, C-367, C-370-372, C-396-398, C-455, C-506, D-189-190, dated 1973-1974.

(56) References Cited

OTHER PUBLICATIONS

Arnold H. Johnson, Ph. D. and Martin S. Peterson, Ph. D., AVI Publishing Company, Inc., Westport, CT, Encyclopedia of Food Technology, vol. 2, p. 818-828, dated 1974.

Allan K. Smith, Ph. D. and Sidney J. Circle, Ph. D., AVI Publishing Company, Inc., Westport, CT, Soybeans: Chemistry and Technology, vol. 1, p. 73-74, 438-441, dated 1978.

T.H. Ferrigno, Reinhold Publishing Corporation, New York, NY, Rigid Plastics Foams, 2nd Edition, p. 2-5, dated 1967.

Erickson, David R. et al., Composition of Soybean Oil, Handbook of Soy Oil Processing and Utilization, American Soybean Association, Chapter 2, p. 13-19, Champaign, IL, 1980.

Zoran S. Petrovic, Andrew Guo and Wei Zhang, Structure and Properties of Polyurethanes Based on Halogenated and Nonhalogenated Soy-Polyols, Journal of Polymer Science: Part A: Polymer Chemistry, vol. 38, p. 4062-4069, dated Aug. 21, 2000.

Andrew Guo, Ivan Javni and Zoran Petrovic, Rigid Polyurethane Foams Based on Soybean Oil, Journal of Applied Polymer Science, vol. 77, p. 467-473, dated Nov. 8, 1999.

Petrovic, Zoran et al., Effect of Structure on Properties of Soy-Based Polyols and Polyurethanes, Pittsburg State University, Kansas Polymer Research Center 2000.

Reed, David, Crain Communications, Renewable Raw Materials— An Important Basis for Urethane Chemistry, Urethanes Technology, vol. 14, No. 2, p. 20-24, dated Apr./May 1997.

Armisted et al. Morphology of Water-Blown Flexible Polyurethane Foams, Journal of Applied Polymer Scuence, vol. 35, p. 601-629, dated 1988.

Christenson et al., Model/MDI/Butendiol Polyurethanes: Molecular Structure Morphology, Physical and Mechanical Properties, Journal of Polymer Science; Part B: Polymer Physics, vol. 24, p. 1401-1439, dated Jul. 1986.

M.D. Bhabhe and V.D. Athawate, Chemoenzymatic Synthesis of Urethane Oil Based on Special Functional Group Oil, Journal of Applied Polymer Science, vol. 69, p. 1451-1458, 1998.

Nakamura et al., Preparation of Polyurethane Foam from Waste Vegetable Oil, translated by the Ralph McElroy Translation Company, vol. 50 (11), p. 881-886, 1993.

Colvin et al., UTECH Asia, Low Cost Polyols from Natural Oils, Paper 36, 1995.

Fe-TAML activators developed at Carnegie Mellon work with oxygen in unprecedented chemistry, Science Blog from Carnegie Mellon University, Sep. 2003.

Weise, Elizabeth, "Green" peroxide catalyst could help clean up the world, www.usatoday.com, Sep. 15, 2003.

Franzen, Harold, Magic Beans for Building, Popular Science, dated Feb. 2002.

Taylor, W.L., Blowing Drying Oils, The Journal of the American Oil Chemists' Society, Minneapolis, Minnesota, p. 472-476, dated Nov. 1950.

\* cited by examiner

US 9,045,581 B2

POLYOLS DERIVED FROM A VEGETABLE OIL USING AN OXIDATION PROCESS

CROSS REFERENCE TO RELATED APPLICATION

This application is a Divisional of application Ser. No. 11/368,159, now U.S. Pat. No. 7,989,647, entitled NOVEL POLYOLS DERIVED FROM A VEGETABLE OIL USING AN OXIDATION PROCESS, filed on Mar. 3, 2006, the disclosure of which is hereby incorporated by reference in its entirety. U.S. application Ser. No. 11/368,159 claims priority to and the benefit of U.S. Provisional Application Ser. No. 60/658,230, filed on Mar. 3, 2005, entitled NOVEL POLYOLS DERIVED FROM A VEGETABLE OIL USING AN OXIDATION PROCESS, the disclosure of which is hereby incorporated by reference in its entirety.

BACKGROUND OF THE INVENTION

Because of their widely ranging mechanical properties and their ability to be relatively easily machined and formed, polyurethane materials, such as urethane elastomers and foams, have found wide use in a multitude of industrial and consumer applications.

The production of urethane polymers is well known in the art. Urethanes are formed when isocyanate (NCO) groups react with hydroxyl (OH) groups. The most common method of urethane production is via the reaction of a petroleum-derived polyol and an isocyanate, which forms the backbone urethane group. Polyester polyols and polyether polyols are the most common polyols derived from petroleum used in urethane production. Polyols are polyhydric alcohols, i.e., alcohols that contain two or more hydroxyl groups.

Sole use of polyols derived from petrochemicals such as polyester or polyether polyols in forming urethane products such as elastomers and foams is disadvantageous for a variety of reasons. Petrochemicals are ultimately derived from petroleum. Accordingly, the petrochemicals are a non-renewable resource. The production of a petroleum-derived polyol requires a great deal of energy, as oil must be drilled, extracted from the ground, transported to refineries, refined, and otherwise processed to yield the polyol. These efforts add to the cost of polyols and to the disadvantageous environmental effects of its production. Also, the price of petroleum-derived polyols tends to be somewhat unpredictable as it tends to fluctuate based on the fluctuating price of petroleum.

Also, as the consuming public becomes increasingly aware of environmental issues, there are distinct marketing disadvantages to petrochemical based products. Consumer demand for "greener" products continues to grow. As a result, it would be most advantageous to replace all or at least some of the polyester or polyether polyols, as used in the production of urethane polymers, with a more versatile, renewable, less costly, and more environmentally friendly component, such as vegetable oil-derived polyols.

One difficulty with the use of vegetable oil-derived polyols to produce a urethane product is that conventional methods of preparing polyols from vegetable oils, such as soybean oils, do not produce polyols having a significant content of hydroxyl groups. Accordingly, it would be advantageous to develop a method to produce vegetable oil-based polyols having increased reactive hydroxyl groups over conventional polyols derived from a vegetable oil such as blown vegetable oil.

Another difficulty with the use of vegetable oil-derived polyols to produce a urethane product is higher than desired residual acid values of the polyol, especially in blown soybean oil polyols (typical blown soybean oil-derived polyol, the residual acid value of a soybean oil-derived polyol ranges from about 5.4 mg KOH/gram to about 7.4 mg KOH/gram). Generally, in the production of urethane elastomers and foams, the residual acid present in vegetable oil-derived polyols retards isocyanate activity by interfering with the isocyanate/alcohol reaction. Also, where the catalyst used to produce urethane polymers is an amine, it is believed that the residual acid can neutralize the amine, making the catalyst less effective. Accordingly, it would be advantageous to develop a method to neutralize the residual acid of the polyol to form reactive hydroxy (OH) groups while not adversely impacting performance of the polyol. A lower acid vegetable oil-derived polyol would be desirable because the lower acid value would improve the performance of polyols in the production of urethane polymer, lower polyurethane catalyst requirements, and improve urethane physical properties due to improved polymer network formation. Accordingly, a significant need exists for low acid, higher functional polyols derived from vegetable oil, especially polyols derived from soybean oil, typically blown soybean oil, and a method for producing such lower acid, higher functional polyols.

BRIEF SUMMARY OF THE INVENTION

One embodiment of the present invention generally relates to a method for making polyols derived from vegetable oil where the polyols have increased hydroxyl functionality where a vegetable oil, typically soybean oil, is reacted with an oxidizing agent in the presence of an organometallic catalyst and the resulting higher functional polyols derived from vegetable oil produced by the process.

Another embodiment of the present invention generally relates to lower acid, higher functionality polyols derived from a vegetable oil and a new method for decreasing the acid value of a polyol by reacting a vegetable oil-derived polyol having increased functionality formed by reacting the vegetable oil, typically a blown soybean oil, with an oxidizing agent in the presence of an organometallic (tetra amido macrocylic ligand) catalyst with an epoxide component in the presence of a Lewis base catalyst.

The present invention further generally relates to the use of (1) the higher functional polyol derived from a vegetable oil, typically a refined and bleached vegetable oil, formed by reacting an oxidizing agent with the vegetable oil in the presence of an organometallic catalyst and/or (2) the lower acid, higher functional vegetable oil-derived polyols as the polyol or one of various polyols and/or as a component of a prepolymer in the production of urethane material, including foams and elastomers. The polyols may be one of the components of the B-side, which can be reacted with an A-side that typically includes a prepolymer (traditional petroleum-derived prepolymer or a prepolymer incorporating a polyol at least partially derived from a vegetable including a lower acid vegetable oil-derived polyol) or an isocyanate.

Another embodiment of the present invention includes the use of the higher functional, typically also lower acid polyols derived from vegetable oil as one of the B-side components (other polyols derived from petroleum may also be used in combination with the higher functional polyols of the present invention as polyol components of the B-side) that is reacted with an A-side that includes an isocyanate and/or a prepolymer, such as the prepolymers discussed above, to form a urethane material. The urethane materials can be used as a precoat and for a backing material for carpet, building composites, insulation, spray foam insulation, other urethane applications such as those requiring use of impingement mix spray guns, urethane/urea hybrid elastomers, vehicle bed liners, flexible foams (furniture foams, vehicle component foams), integral skin foams, rigid spray foams, rigid pour-in-place foams, coatings, adhesives, sealants, filament winding, and other urethane composites, foams, elastomers, resins, and reaction injection molding (RIM) applications.

These and other features, advantages, and objects of the present invention will be further understood and appreciated by those skilled in the art by reference to the following specification, claims, and appended drawings.

DETAILED DESCRIPTION OF PREFERRED EMBODIMENT

Applicant has surprisingly discovered that oxidation of a vegetable oil, most typically soybean oil, in the presence of an organometallic catalyst, typically a TAML® (tetra amido macrocyclic ligand) catalyst, results in a vegetable oil-derived polyol having increased hydroxyl group functionality. A method for producing vegetable oil-derived polyols with increased functionality having lower acid values has also been developed.

The method for making a vegetable oil-based polyol with increased functionality generally includes reacting a vegetable oil, typically soybean oil, more typically a refined, bleached soybean oil, with an oxidizing agent in the presence of an organometallic (tetra amido macrocyclic ligand) oxidation catalyst. Generally, the oxidation reaction occurs at elevated temperatures of from about 95° C. to about 150° C., more typically from about 95° C. to about 110° C., and most typically about 95° C. However, it is presently believed that the oxidation reaction may function at temperatures of about 50° C. or greater. This oxidation process yields a polyol with a hydroxyl value ranging from about 56 mg KOH/gram polyol to about 220 mg KOH/gram polyol. More typically, this oxidation process yields a polyol with a hydroxyl value ranging from about 112 mg KOH/gram of polyol to about 220 mg KOH/gram polyol.

Oxidation Reaction

In the oxidation reaction of one embodiment of the present invention, the oxidizing agent is typically a chemical which can act as an electron receptor or is a substance in an oxidation-reduction reaction that gains electrons and whose oxidation number is reduced. Typically, hydrogen peroxide or air and most typically hydrogen peroxide is utilized. However, it is presently believed that oxidizing agents can include all organic peroxides. Typically, where the oxidizing agent is air, dried air is preferably introduced at a rate of about 300 cubic feet per minute (CFM) for the volume of oil used. Where the oxidizing agent is hydrogen peroxide, a solution of from about 35% to about 50% hydrogen peroxide is preferably used. A higher concentration of hydrogen peroxide is generally preferred in order to maximize contribution to the reaction of the oxidizing agent and for completion of the reaction. Preferably, the hydrogen peroxide solution is utilized in amounts ranging from about 10% by weight to about 50% by weight of the reaction material.

Typically, the polyol is a polyol at least partially derived from a vegetable oil, typically a soybean oil, a rapeseed oil, a palm oil, a safflower oil, a sunflower oil, a corn oil, a linseed oil, a tall oil, a toung oil, a canola oil, or a cottonseed oil, more typically a refined, bleached soybean oil, and most typically a refined, bleached soybean oil produced according to the process disclosed in U.S. Pat. Nos. 6,476,244 and 6,759,542, the disclosures of which are incorporated by reference in their entirety.

The vegetable oil-derived polyol, typically a polyol derived from soybean oil, is oxidized in the presence of an organometallic catalyst, typically a TAML® (tetra amido macrocyclic ligand) catalyst, most typically Fe-TAML® (iron tetra amido macrocyclic ligand) catalyst. Tetra amido macrocyclic ligand is an environmentally friendly catalyst that causes an oxygen component to work faster and more safely. Specifically, where the oxidizing agent is hydrogen peroxide, the tetra amido macrocyclic ligand catalyst forms activated peroxides that are very reactive, but more selective than free radicals formed during the normal decomposition of hydrogen peroxide. The structure of a tetra amido macrocyclic ligand catalyst is shown below. It is currently believed that an inorganic metal tetra amido macrocyclic ligand activated peroxide complex, typically one based on an iron tetra amido macrocyclic ligand, associates with double bonds on the soybean oil to form hydroxyl groups at the available vinylic sites of the vegetable oil. In the oxidation reaction of one embodiment of the present invention, the amount of the tetra amido macrocyclic ligand catalyst used is typically from about 0.2 ppm to about 200 ppm of catalyst used in the reaction, preferably from about 0.2 to about 2.0 ppm, and most preferably about 0.2. However, it is presently believed that the amount of tetra amido macrocyclic ligand catalyst may be 0.01 ppm or greater.

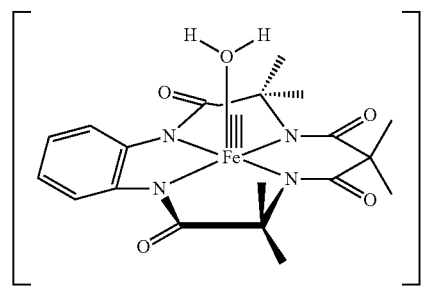

Applicants have surprisingly discovered that oxidizing a vegetable oil, most typically a soybean oil, in the presence of an organometallic catalyst, typically a tetra amido macrocyclic ligand catalyst, most typically an Fe— (tetra amido macrocyclic ligand catalyst), results in a vegetable oil-derived polyol having increased hydroxyl group functionality of about 56 mg KOH/gram polyol to about 220 mg KOH/gram polyol, more typically of greater than 85 mg KOH/gram polyol as compared to vegetable oil oxidized by blowing processes, which typically yields a polyol with a hydroxyl value ranging from about 56 mg KOH/gram polyol to about 80 mg KOH/gram polyol.

The following examples demonstrate the oxidation of a vegetable oil, typically soybean oil, in the presence of a tetra amido macrocyclic ligand catalyst to form a vegetable oil-derived polyol having increased hydroxyl functionality.

The following general experimental procedure and sample analysis was used for all example oxidation reactions discussed below. In a multi-neck reactor flask equipped with an agitator blade on a stir shaft connected to a stir motor, a quantity of refined, bleached soybean oil was heated. One neck of the flask was equipped with a 300 mm vigreaux column packed with glass beads beneath a water-cooled side-arm condenser so that distillate could be collected and vacuum distillation could be performed at the end of reaction if desired. A temperature probe and nitrogen inlet were present in the flask. The soybean oil was heated to a desired reaction temperature, typically a temperature of from about 95° C. to about 130° C., before adding the tetra amido macrocyclic ligand catalyst. In air oxidation experiments, dried air was incorporated into the reaction mixture through a stainless steel sparger tube at a rate equivalent to 300 cubic feet per minute for the volume of oil used. In hydrogen peroxide oxidation experiments, the peroxide solution was added in increments specified in each reaction.

Periodic samples were removed from the flask while the reaction mixture was stirred. To indicate the presence or absence of peroxide in the reaction mixture samples, sodium bisulfite was added to the sample. If peroxides are present, they react with the bisulfite to generate $SO_2$ gas in a vigorous, bubbling, exothermic reaction. Even a mild reaction between bisulfite and peroxide can be detected by suspending a strip of pH paper above a beaker containing the reactants (pH paper turns red in the presence of the acidic gas). Bisulfite was effective in neutralizing peroxides in reaction samples; however, the presence of bisulfite interfered in hydroxyl titrations. When possible, samples were analyzed before adding large quantities of peroxide to minimize the effect of peroxides and moisture on titrations. Samples containing considerable quantities of water were allowed to phase separate before analyzing the oil/polyol fraction.

Titrimetric analytical methods were used to track reaction progress in these reactions. Analytical methods include hydroxyl titration (ASTM D 4274-99, B), acid value titration (ASTM D 4662-03, A), and viscosity (ASTM D 4878-03, A).

The following oxidation reactions were conducted using 300 CFM (cubic feet per minute) dried air for the volume of oil used.

TABLE 1

|  | Experiment No. | | |
|---|---|---|---|
|  | 1 | 2 | 3 |
| Weight soybean oil (grams) | 502.62 | 506.31 | 500 |
| TAML ® concentration (ppm) | 100 | 100 | 50 |
| Temperature (° C.) | 115 | 115 | 115 |
| Total reaction time (hours) | 42 | 27 | 35 |
| Final viscosity (cPs) | 20636 | 2257 | 7693 |
| Final acid value (mg KOH/gram sample) | 11.31 | 7.9 | 8.82 |
| Final corrected hydroxyl value (mg KOH/gram sample) | 65.9 | 64.9 | 71.47 |

The following oxidation reactions were carried out using hydrogen peroxide as the oxygen component.

TABLE 2

| Experiment No. | 1 | 2 | 3 | 4 | 5 | 6 |
|---|---|---|---|---|---|---|
| Weight soybean oil (grams) | 500 | 500 | 515.8 | 500 | 500 | 800 |
| TAML ® concentration (ppm) | 50 | 50 | 5 | 5 | 5 | 1 |
| Hydrogen peroxide concentration (%) | 50 | 50 | 35 | 50 | 50 | 50 |
| Weight of hydrogen peroxide (grams) | 338.56 | 388.56 | 496.6 | 347.6 | 347.6 | 556.2 |
| Temperature (° C.) | 110 | 110 | 110 | 110 | 130 | 110 |
| Total reaction time (hours) | 20 | 96 | 140 | 81 | — | 64 |
| Final acid value (mg KOH/gram sample) | 1.13 | 24.21 | — | 3.86* | — | 1.16* |

TABLE 2-continued

| Experiment No. | 1 | 2 | 3 | 4 | 5 | 6 |
|---|---|---|---|---|---|---|
| Final corrected hydroxyl value | 10.26 | 127.04 | 67.23 | 172.12* | — | 143.3* |

*Final acid values and final corrected hydroxyl values were measured after the resulting vegetable oil-derived polyol was subjected to the residual acid reduction method described below.

Residual Acid Value Reduction

One potential drawback of using the tetra amido macrocyclic ligand catalyst process described above to form highly functionalized polyols derived from vegetable oil is the fact that the process tends to produce a polyol with high residual acid values. High residual acid values in polyols are undesirable in most all applications because the acids inhibit catalysts and urethane reaction rates. Applicants have discovered that a higher residual acid value, high functionality polyol is well suited for use as a replacement for some (or all) of the polyols derived from petroleum when urethanes are used in applications, longer pot life reactions yield better products and provide greater processing flexibility. However, for a majority of urethane applications, the residual acid values are undesired. Accordingly, Applicants have discovered a process to lower the residual acid value of the higher functional polyols.

A vegetable oil-derived polyol of one embodiment of the present invention formed by oxidation of a vegetable oil, typically soybean oil, in the presence of an organometallic catalyst, typically a TAML® catalyst, may further be reacted with an epoxide component to reduce the amount of residual acid present in the polyol. As used herein, the "acid value" of an acid-functional polyol is a measurement of the amount of base, typically sodium hydroxide (NaOH), necessary to neutralize the residual acid present in the polyol. It is presently believed that the residual acid is the result of either decomposition of triglyceride ester bonds into free fatty acids or oxidizing alcohols into carboxylic acids. The acid value is determined by weighing a small sample, typically from less than one gram to about 10 grams, more typically from about 2 to about 10 grams, of the polyol into a flask. A solvent, typically acetone or a mixture of acetone and isopropyl alcohol in a 1:1 ratio, is added to the flask to dissolve the polyol. The solution is titrated with a standardized solution of sodium hydroxide (NaOH) and reported in units of milligrams KOH per gram of sample. The acid value of a typical blown soybean-derived polyol typically ranges from about 5.4 mg KOH/gram to about 7.4 mg KOH/gram.

The polyol derived from vegetable oil or a polyol derived from a blown soybean oil polyol, which may or may not have been reacted with the tetra amido macrocyclic ligand catalyst as described above, is reacted with an epoxide component. An epoxide is an organic group containing a reactive group characterized by the union of an oxygen atom with two other atoms, typically carbon, to form:

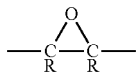

wherein R is either H or an organic group.

In this embodiment of the present invention, any epoxide can be reacted with a polyol derived from vegetable oil. Typically, the epoxide utilized is neodecanoic acid 2,3-epoxypropylester. Other epoxides that may be utilized include polyglycol di-epoxides such as D.E.R.™ 736 available from Dow Chemical of Midland, Mich., and glycidyl esters and glycidyl epoxy ether such as CARDURA™ E10P, available from Resolution Performance Products of Houston, Tex. Alternatively, a mixture of epoxides may be used in this embodiment of the present invention. The amount of epoxide used in the reaction typically ranges from about 90% to about 500% of the stoichiometric molar amount of acid in carboxylic groups present in the vegetable oil-derived polyol.

The vegetable oil-derived polyol and the epoxide are typically reacted in the presence of a Lewis base catalyst or mixture of Lewis base catalysts. The Lewis base catalyst used to neutralize residual acid in the polyols derived from vegetable oil, typically blown soybean oil polyol, in this embodiment of the present invention are Lewis base catalysts that are generally known in the art. Examples of Lewis base catalyst that may be used include: tertiary amines such as DABCO 33-LV® comprised of 33% 1,4-diaza-bicyclo-octane (triethylenediamine) and 67% dipropyleneglycol, a gel catalyst available from the Air Products Corporation of Allentown, Pa.; DABCO® BL-22, a tertiary amine also available from the Air Products Corporation; POLYCAT® 41 trimerization catalyst (N,N',N''-dimethylaminopropylhexahydrotriazine) available from the Air Products Corporation; and Air Products DBU® (1,8 diazabicyclo [5.4.0]). Dimethylethanolamine (DMEA) and triphenylphosphine (TPP) may also be used as the Lewis base catalyst. Other catalysts that can be used in the present invention include such compounds as the amines, mono-, di- and tri-aliphatic and alkanol amines, pyridines, piperidines, aromatic amines, ammonia, ureas, quinolines, imidazoles and imidazolines and other heterocyclic nitrogen compounds and the like. Examples include aniline, triethylene diamine, imidazole, piperidine, pyrrolidine and diethanolamine. Another class of such Lewis base catalysts are organometallic compounds such as dibutyl tin oxide, monobutyl tin chloride, triphenyl phosphine and other organometallic compounds with unshared electron pairs such as metal carbonyls and phosphine or phosphite complexes, e.g. iron pentacarbonyl. Especially preferred are the organotin Lewis base catalysts, more specifically dibutyl tin oxide and monobutyl tin chloride, and the N-substituted tetra(lower alkyl) ureas, more specifically N,N,N',N' -tetramethyl urea.

The Lewis base catalysts used to produce lower acid vegetable oil-derived polyols are also catalysts in the preparation of urethanes, so it may be acceptable to use an amount in excess of what is necessary for the polyol-epoxide reaction. However, too great an excess of Lewis base catalyst is not preferred because too much Lewis base catalyst may negatively affect the color, odor, and viscosity of the resulting polyol. In one embodiment of the present invention, the Lewis base catalyst is typically present in an amount of from about 0.1 weight percent to about 0.3 weight percent relative to epoxide content used in the reaction.

The polyol-epoxide reaction typically occurs at elevated temperatures. The reaction temperature is typically from about 110° C. to about 160° C., more typically from about 130° C. to about 150° C. The polyol-epoxide reaction mixture may also be agitated and nitrogen sparged. Generally, nitrogen sparging is the process of bubbling gaseous nitrogen through a liquid reaction. Nitrogen sparging replaces the amount of air initially present and thus, acts to reduce contact with water present in the air initially entrained in polyols derived from vegetable oils.

Lower acid vegetable oil-derived polyols produced using the method of this embodiment of the present invention typically have decreased water content as compared to other polyols produced from blowing soybean oil. It is presently believed that the decreased water content is due to the epoxide reactivity with water in the polyol-epoxide reaction used to produce lower acid vegetable oil-derived polyols. Generally, the epoxide may react with an acid, thereby reducing the residual acid in polyols derived from vegetable oils, or with an alcohol (OH). The OH can come from the polyol or from water. Accordingly, the epoxide reacts with the water to decrease the water content in the polyol derived from vegetable oil, typically soybean oil. Typically, a maximum water content of 0.10 can be reduced by about 20% to about 30% to a water content of about 0.07 to about 0.08.

Using the methods of this embodiment of the present invention, the acid value of a polyol derived from soybean oil decreases from initial values of from about 5.4 milligrams KOH/gram polyol to about 7.4 milligrams KOH/gram polyol to values from about 1.0 milligram KOH/gram polyol to about 3.0 milligrams KOH/gram polyol. Polyol-epoxide reaction time typically ranges from about 15 minutes to about 40 hours, more typically from about 30 minutes to about 2 hours. The polyol-epoxide reaction time is a digestion process time and does not include the reaction time required to create the vegetable oil-derived polyol, typically a blown soybean oil polyol or other blown vegetable oil polyol, or the vegetable-oil derived polyol produced by the oxidation process described herein.

Preparation of Urethane Products Using Novel Polyols Derived from a Vegetable Oil Lower acid value polyols derived from vegetable oil, most typically polyols derived from blown soybean oil made in accordance with the method discussed above, may be used to prepare any urethane product. The lower acid polyols of the present invention may even be used to replace some or all of the petroleum-based polyols, for example, in reaction injection molding processes and the other processes discussed herein. The lower acid polyols of one embodiment of the present invention may be one of the components of the B-side in urethane reactions generally, which are reacted with an A-side that typically includes a prepolymer (a traditional petroleum-derived prepolymer or a prepolymer incorporating a polyol at least partially derived from a vegetable oil, such as described in U.S. Pat. Nos. 6,624,244; 6,864,296; 6,881,763; and 6,867,239, which are hereby incorporated by reference in their entireties and, including a lower acid vegetable oil-derived polyol) and/or an isocyanate to form a polyurethane product.

Polyurethanes can be prepared in a one-step or a two-step process. In the one-step process, an A-side reactant is combined with a B-side reactant. The A-side typically includes an isocyanate or a mixture of isocyanates or prepolymer or mixtures of prepolymers and isocyanates. The A-side isocyanate reactant of the urethane is preferably comprised of an isocyanate chosen from a number of suitable isocyanates as are generally known in the art. Different isocyanates may be selected to create different properties in the final product. The A-side reactant of the urethane typically includes one or more of the following diisocyanates: 4,4'-diphenylmethane diisocyanate; 2,4-diphenylmethane diisocyanate; and modified diphenylmethane diisocyanate. Typically, a modified diphenylmethane diisocyanate is used. Mixtures of different isocyanates may also be used.

The A-side of the reaction may also be a prepolymer isocyanate alone or in combination with an isocyanate. The prepolymer isocyanate is typically the reaction product of an isocyanate component, preferably a diisocyanate, and most preferably some form of diphenylmethane diisocyanate, and a polyol component. The polyol component may be derived from a petroleum oil (such as polyether and/or polyester polyols), vegetable oil or a combination of petroleum and vegetable oil-derived polyols. Applicants have surprisingly discovered that less petroleum oil-derived polyol can be used when the vegetable oil-derived polyol is a lower acid vegetable oil-derived polyol. The polyol derived from vegetable oil may be based upon blown or unblown soybean oil, rapeseed oil, cottonseed oil, palm oil, any other vegetable oil discussed herein, or any other vegetable oil having a suitable number of reactive sites. The most preferred vegetable oil used to derive the polyol is soybean oil, in particular, a refined and bleached soybean oil. There will still be unreacted isocyanate groups in the prepolymer. However, the total amount by weight of reactive A-side material has increased through this process. The prepolymer reaction reduces the cost of the A-side component by decreasing the amount of isocyanate required and utilizes a greater amount of inexpensive, environmentally friendly polyol derived from vegetable oil, preferably soybean oil. In order to permit the prepolymer diisocyanate A-side to react with the B-side, additional isocyanate typically must be added to elevate the isocyanate level to an acceptable level.

The A-side of one embodiment of the present invention may optionally include an isocyanate (a first isocyanate) and a prepolymer comprising the reaction product of a second isocyanate and a first polyol at least partially derived from a vegetable oil, or a combination of various isocyanates and prepolymers. Any suitable isocyanate may be used for the purposes of the present invention. One polyisocyanate component particularly suitable for use in the reaction system of the present invention is RUBINATE® M. RUBINATE® M is an MDI (methylenebisdiphenyl diisocyanate), which is commercially available from Huntsman Chemicals of Salt Lake City, Utah.

The B-side material is generally a solution of at least one polyol such as in one embodiment of the present invention, the lower acid oxidized soybean oil polyol described above a cross-linking agent and/or a chain extender, and optionally a catalyst. If preparing a polyurethane foam, a blowing agent using a chemical or physical blowing agent is typically also used. When a catalyst is added to the B-side, it is added to control reaction speed and affect final product qualities.

Polyurethane elastomers and urethane foams can be prepared using lower acid vegetable oil-derived polyols in the B-side preparation alone or in the presence of a multi-functional alcohol, cross-linking agent, or chain extender. Alternatively, a blend of traditional petroleum-based polyol and lower acid vegetable oil-derived polyols may be used alone or in the presence of a multi-functional alcohol, cross-linking agent, or chain extender.

The B-side reactant of the urethane reaction in one embodiment of the present invention typically includes a vegetable oil-based polyol and a multifunctional, active hydrogen-containing compound, typically a chain extender and/or a cross-linking agent. Multifunctional alcohols are possible active hydrogen-containing compounds. Typically, a catalyst is also included in the B-side. Examples of catalysts that may be utilized include tertiary amines such as DABCO 33-LV® comprised of 33% 1,4-diaza-bicyclo-octane (triethylenediamine) and 67% dipropyleneglycol, a gel catalyst available from the Air Products Corporations of Allentown, Pennsylvania; DABCO® BL-22, a tertiary amine available from the Air Products Corporation; POLYCAT® 41 trimerization catalyst (N,N',N"-dimethylaminopropylhexahydrotriazine) available from the Air Products Corporation; and Air Products DBU® (1,8 diazabicyclo [5.4.0]). These catalysts may also be used as Lewis base catalysts in the polyol-epoxide reaction used to form lower acid vegetable oil-derived polyols. While the level of catalyst used in the process of lowering the residual acid value of the polyol is typically in amounts sufficient to at least substantially lower the acid value of the polyol, an excess amount can also be utilized. Typically, the amount of Lewis base catalyst to be used should be approximated such that the residual acid value of the polyol is reduced as far as possible while not utilizing such an amount of Lewis base catalyst that substantial excess remains. Accordingly, while excess Lewis base material may be utilized, an excess of catalyst is generally not preferred because the presence of too much catalyst may begin to affect the color, odor, and viscosity of the lower acid vegetable oil-derived polyol used to produce urethane.

A blowing agent is typically included in the B-side of the reaction of one embodiment of the present invention when preparing a urethane foam material or similar product. Blowing agents useful in the present invention include both chemical and physical blowing agents such as air, water, 134 A refrigerant available from Dow Chemical Co. of Midland, Mich., methyl isobutyl ketone (MIBK), acetone, methylene chloride, a hydroflurocarbon (HFC), a hydrochloroflurocarbon (HCFC), cycloaliphatic hydrocarbons such as cyclopentane, an aliphatic hydrocarbon such as normal or isopentane, or mixtures thereof. For carpet applications, air, sometimes referred to in the carpet industry as frothing, or water are the presently preferred blowing agents. The concentrations of other reactants may be adjusted to accommodate the specific blowing agent and the desired end properties of the reaction product. These blowing agents create gas bubbles in the reacting mass.

Cross-linking agents and chain extenders used in the B-side reactant of the urethane reaction are at least difunctional (typically at least a diol). Typical cross-linking agents and chain extenders include ethylene glycol and 1,4-butanediol; however, other diols or higher functional alcohols such as glycerin may be used.

When preparing a urethane foam using lower acid vegetable oil-derived polyols, the B-side reactant may optionally further comprise a silicone surfactant, which functions to influence liquid surface tension and thereby influence the size and stability of the bubbles that are formed and ultimately the size of the hardened void cells in the final foam product. This results in more uniform foam density, increased rebound, and a softer foam. Also, the surfactant may function as a cell opening agent to cause larger cells to be formed in the foam.

The use of vegetable oil-derived polyols, including lower acid vegetable oil-derived polyols, to prepare polyurethane products, including elastomers and foams, realizes a significant cost savings because some or all of the more costly petroleum-based polyols may be replaced when forming urethane products by any known method. Vegetable oils are abundant, renewable, and easily processed commodities, as opposed to petroleum-based polyols which entail significant associated processing costs. There is a distinct marketing advantage to marketing products that are based on environmentally friendly, renewable resources such as vegetable oils.

Lower acid value polyols derived from vegetable oil, most typically polyols derived from soybean oil, made in accordance with one embodiment of the present invention increase available end uses and improve the performance of polyols within current end uses. For example, the lower acid, higher functionality polyols can be used to produce rigid polyisocyanurate foams such as pour-in-place foams, discontinuous metal panels, laminated boardstock and bunstock foams. As already noted, it is believed that the residual acid retards isocyanate activity in the formation of polyol-based polyurethanes by interfering with the isocyanate/hydroxyl reaction to form urethane, urea, and/or isocyanurate polymers. Also, it is believed that residual acid retards isocyanate reactivity by neutralizing the catalyst. Accordingly, the improvement in performance is a direct result of the decreased residual acid content of the polyol and results in faster reactivities and/or lower polyurethane catalyst requirements in formulations using polyols derived from blown vegetable oils, typically polyols derived from blown soybean oil. It is presently believed that improvements in physical properties dependent upon flow, adhesion to surfaces, wet out, or processing of polyurethane formulations containing such polyols derived from vegetable oil will also occur. It is expected that using the lower acid vegetable oil-derived polyols of one embodiment of the present invention will also improve the K-factor, a measurement of the thermal conductivity for a unit thickness of material. Also, use of polyols derived from vegetable oil in polyurethane formulations will result in improved density distribution and consistent spherical cell size across the material end product, creating enhanced dimensional stability.

As briefly discussed above, the higher functionality polyols of one embodiment of the present invention which are derived from vegetable oil that has been reacted with an oxidizing agent in the presence of TAML® catalyst are especially useful in a polyurethane pultrusion process because the higher acid value lowers the reaction rate of the urethane, a property which is very helpful in processing pultrusion applications.

The polyol at least partially derived from a vegetable oil of the B-side in one embodiment of the present invention is typically blown vegetable oil, most typically blown soybean oil, blown rapeseed oil, blown cottonseed oil, blown safflower oil, blown palm oil, or blown canola oil. Specific polyols derived from vegetable oil that may be utilized include SOYOL™ P38N and SOYOL™ R2-052 polyols, both available from Urethane Soy Systems Company of Volga, S. Dak. These polyols are nominal two functional polyols made from unmodified soybean oil and have a hydroxyl value of 52 to 56 mg KOH/gram polyol, typically 54 mg KOH/gram polyol, an acid value of 5.4 to 7.4 mg KOH/gram polyol, typically 6.4 mg KOH/gram polyol, a viscosity of 2500 cPs to 4000 cPs, typically 3000 cPs, and a moisture content of less than 0.10 weight percent. Another example is SOYOL™ R3-170 polyol, which is also available from Urethane Soy Systems Company, and which is a nominal three functional polyol made from unmodified soybean oil and having a hydroxyl value of 160 mg KOH/gram to 180 mg KOH/gram, typically 170 mg KOH/gram, an acid value of 5.0 mg KOH/gram to 7.3 mg KOH/gram, a viscosity of 3000 cPs to 6000 cPs at 25° C., and a moisture content of less than 0.10 weight percent. SOYOL™ R2-052C polyol is a polyol derived from soybean oil that exhibits a low viscosity, typically measuring 800 cPs to 1200 cPs at 25° C. on the viscometer.

The polyol(s) at least partially derived from vegetable oil may be utilized in place of some or all of the polyols derived from petroleum in pultrusion systems, thus providing a renewable resource in the final polymer composite. The polyol at least partially derived from vegetable oil, as discussed above, is typically a blown vegetable oil which can be further modified by other processes. It has been surprisingly discovered that the process of blowing soybean oil causes formation of fatty acids. Typically, acids are undesirable in a polyol component to be used in the formation of urethane materials because the acid components interfere and, as a result, slow the urethane reaction rate and thereby affect the formation of the final urethane material. However, slower reaction rates are desired in the case of continuous processes using snap-cure urethane chemistry because it significantly improves processing and thus provides the ability to pultrude the material at a faster rate than conventional urethane pultruded materials.

The B-side of the present invention may optionally further include a polyol derived from petroleum or other polyol. An example of two particularly preferred polyether polyols for use in the present invention are the propylene oxide adducts of glycerol, commercially available as JEFFOL® G30-650 and JEFFOL® G30-240 polyols. JEFFOL® G30-650 is a propoxylated glycerol with a hydroxyl value of about 650 mg KOH/gram available from Huntsman Petrochemical Corporation of Salt Lake City, Utah and JEFFOL® G30-240 is a propoxylated glycerol with a hydroxyl value of about 240 mg KOH/gram, also available from Huntsman.

The B-side of one embodiment of the present invention may optionally further include a second polyol derived from petroleum such as a sucrose based polyether polyol. One such polyether is MULTRANOL® 9171, which is a sucrose based polyether polyol with a molecular weight of about 1,020. The MULTRANOL® 9171 has a hydroxyl number range of from about 330 mg KOH/gram to about 350 mg KOH/gram, a water content of less than 0.10 weight percent, an acid number of less than 0.10 mg KOH/gram (max.), and a viscosity range of from about 7,000 cPs to about 11,000 cPs at 25° C. MULTRANOL® 9171 is typically a clear or amber viscous liquid which is slightly hygroscopic and may absorb water. MULTRANOL® 9171 is commercially available from Bayer Corporation, Polymers Division, located at 100 Bayer Road, Pittsburgh, Pa.

The B-side of one embodiment of the present invention may optionally further include an adhesion promoter, a coupling agent, or a blend thereof. One such adhesion promotor that may be used as a component of the B-side is SILQUEST® A-187 a Gamma-Clycidoxypropyl. SILQUEST®A-187 is commercially available from GE Silicones of Wilton, Connecticut. Other examples of suitable adhesion promoters include amino alkoxy silanes and vinyl alkoxy silanes.

The B-side of one embodiment of the present invention may optionally further include an adhesion promoter, a coupling agent, or a blend thereof. One such adhesion promotor that may be used as a component of the B-side is SILQUEST® A-187 a Gamma-Glycidoxypropyltrimethoxysilane. SILQUEST® A-187 is commercially available from GE Silicones of Wilton, Connecticut. Other examples of suitable adhesion promoters include amino alkoxy silanes and vinyl alkoxy silanes.

The B-side of one embodiment of the present invention may optionally further include a catalyst or a mixture of catalysts. A catalyst is typically used to increase the reaction rate of the polyol-isocyanate resin, or control the reaction order between competing reactions. An organometallic catalyst that may be utilized is K-KAT® 5218, which is used as an accelerator in the production of composite parts. The K-KAT® 5218 catalytic activity accelerates the reaction of aromatic isocyanates and alcohols. K-KAT® 5218 presents an alternative to conventional tin catalysts and can provide unique variations in cure response. K-KAT® 5218 is commercially available from King Industries Inc. of Norwalk, Conn. Other suitable catalysts for use in the present invention include tin catalysts, typically organo tin catalysts; dialkyl tin salts of carboxylic acids; organo titanium catalyst; and mixtures thereof.

The B-side of one embodiment of the present invention may optionally further include a chain extender suitable to extrapolate in a linear fashion due to terminal primary hydroxyl groups. One such chain extender suitable for use in the present invention is 1,4-Butanediol (1,4 BDO). 1,4 BDO is a versatile chemical intermediate because of its terminal primary hydroxyl groups and its hydrophobic and chemical resistant nature. General characteristics of 1,4 BDO include a boiling point (@760 TORR) of 228° C. (442° F.), a freezing point of 19° C. to 20° C., and a hydroxyl value of 1245 mg KOH/gram. 1,4-BDO is available from Lyondell Chemical Company of 1221 McKinney St., Houston Tex. Other suitable chain extenders that may be utilized as components of the B-side include dialkyl substituted methylene dianiline, diethyltoluene diamine, substituted toluene diamines, ethylene glycol, propylene glycol, diethylene glycol, dipropylene glycol, and mixtures thereof.

The B-side of one embodiment of the present invention may optionally further include a multifunctional alcohol and a cross linking agent. For the purposes of this application, a cross linking agent is a triol or higher functional polyol that controls the flexibility, rigidity, and other physical characteristics of the final polymer composite. A multifunctional alcohol suitable for use in the present invention is glycerin or sucrose.

The B-side of one embodiment of the present invention may optionally further include a mold release compound such as an organophosphate ester. Such a compound promotes internal mold release (IMR) of the final polymer composite. TECH-LUBE™ HP-200, available from Technick Products of Rahway, N.J., is a suitable organophosphate ester which may be used as a mold release agent in the present invention. The mold release compound, typically an organophosphate, helps the cured pultruded product release from the heated die without damaging the composite with adhesion to the mold.

The B-side of one embodiment of the present invention may optionally further include a molecular sieve, which functions to seek and eliminate moisture. A preferred molecular sieve for use in the present invention is BAYLITH® L-paste, which serves as a water scavenger. The paste can use castor oil as a carrier. BAYLITH® L-paste is commercially available from Bayer Corporation, located at 100 Bayer Road, Pittsburgh, Pa. BAYLITH® is commonly referred to as Zeolite.

The urethane material may be the reaction product of an A-side and a B-side where the A-side includes a compound having isocyanate reactive groups, such as a methylenebisdiphenyl diisocyanate, and the B-side includes a vegetable oil-derived polyol, typically a soybean oil-derived, oil polyol such as a blown soybean oil polyol; a petroleum-derived polyol; a castor oil; optionally, a chain extender; a multifunctional alcohol, such as a cross-linking agent; optionally, a mold release compound; optionally, a molecular sieve; optionally, a coupling agent; and optionally, an organometallic catalyst. The organometallic catalyst is typically an organometallic oxidation catalyst such as a tetra amido macrocytic ligand catalyst, most typically an iron tetra amido macrocylic ligand catalyst. The B-side may include any of the following specific combinations:

B-side list #1
about 26% by weight of a combination of two vegetable (soybean) oil-derived polyols;
about 35% by weight polyether polyol;
about 23% by weight castor oil;
about 5% by weight chain extender;
about 5% by weight multifunctional alcohol (cross-link agent);
about 3% by weight mold release compound;
about 2% by weight molecular sieve;
about 1% by weight coupling agent; and
about 0.4% by weight organometallic oxidation catalyst.

B-side list #2
about 26% by weight blown soybean oil polyol;
about 35% by weight propaxylated glycerol;
about 23% by weight castor oil;
about 5% by weight 1,4-butanediol;
about 5% by weight glycerin;
about 3% by weight organophosphate ester;
about 2% by weight zeolite;
about 1% by weight silane; and
about 0.4% by weight organometallic oxidation catalyst.

B-side list #3
about 25% by weight vegetable oil-derived polyol;
about 35% by weight polyether polyol;
about 26% by weight castor oil;
about 10% by weight multifunctional alcohol;
about 2% by weight molecular sieve;
about 1% by weight coupling agent; and
about 0.6% by weight organometallic oxidation catalyst.

B-side list #4
about 25% by weight blown soybean oil polyol;
about 35% by weight propoxylated glycerol;
about 26% by weight castor oil;
about 10% by weight glycerin;
about 2% by weight zeolite;
about 1% by weight silane; and
about 0.6% by weight organometallic oxidation catalyst.

B-side list #5
about 26% by weight vegetable (soybean) oil-derived polyol;
about 25% by weight polyether polyol;
about 26% by weight castor oil;
about 5% by weight multifunctional alcohol (cross-linked agent);
about 2% by weight molecular sieve;
about 1% by weight coupling agent; and
about 0.6% by weight organometallic oxidation catalyst, B-side list #6
about 26% by weight blown soybean oil polyol;
about 26% by weight castor oil;
about 15% by weight propoxylated glycerol;
about 10% by weight polyether polyol;
about 5% by weight glycerin;
about 2% by weight zeolite;
about 1% by weight saline; and
about 0.6% by weight organometallic oxidation catalyst Example I is one aspect of the present invention that comprises a formulation of:

EXAMPLE I

B-side:

| Component | Percent by weight |
| --- | --- |
| Blown soybean oil polyol (SOYOL ™ R2-052) | 10 |
| Blown soybean oil polyol (SOYOL ™ R3-170) | 16 |
| Propoxylated glycerol (JEFFOL ® G30-650) | 35 |
| Castor oil | 23 |
| Adhesion Promotor (SILQUEST ® A-187) | 1 |
| Organometallic catalyst (K-KAT ® 5218) | 0.4 |
| Chain extender (1,4 BDO) | 5 |
| Multifunctional alcohol (Glycerin) | 5 |
| Organophosphate ester (TECHLUBE ® HP-200) | 3 |
| Molecular sieve (BAYLITH ® L-paste) | 2 |
| TOTAL: | 100.4 |

A-side:
Component
Specialty isocyanate (RUBINATE® M)

Example II is another aspect of the present invention that comprises a formulation of:

EXAMPLE II

B-side:

| Component | Percent by weight |
|---|---|
| Blown soybean oil polyol (SOYOL ™ P38N) | 25 |
| Propoxylated glycerol (JEFFOL ® G30-650) | 35 |
| Castor oil | 26 |
| Adhesion Promotor (SILQUEST ® A-187) | 1 |
| Organometallic catalyst (K-KAT ® 5218) | 0.6 |
| Multifunctional alcohol (Glycerin) | 10 |
| Molecular sieve (BAYLITH ® L-paste) | 2 |
| TOTAL: | 99.6 |

A-side:
Component
Specialty isocyanate (RUBINATE® M)

Example III is another aspect of the present invention that comprises a formulation of:

EXAMPLE III

B-side:

| Component | Percent by weight |
|---|---|
| Blown soybean oil polyol (SOYOL ™ R2-052C) | 26 |
| Propoxylated glycerol (JEFFOL ® G30-240) | 15 |
| Polyether polyol (MULTRANOL ® 9171) | 10 |
| Castor oil | 26 |
| Adhesion Promotor (SILQUEST ® A-187) | 1 |
| Organometallic catalyst (K-KAT ® 5218) | 0.6 |
| Multifunctional alcohol (Glycerin) | 19 |
| Molecular sieve (BAYLITH ® L-paste) | 2 |
| TOTAL: | 99.6 |

A-side:
Component
Specialty isolyanate (RUBINATE® M 1.5:1

The above description is considered that of the preferred embodiments only. Modifications of the invention will occur to those skilled in the art and to those who make or use the invention. Therefore, it is understood that the embodiments described above are merely for illustrative purposes and not intended to limit the scope of the invention, which is defined by the following claims as interpreted according to the principles of patent law, including the doctrine of equivalents

The invention claimed is:

1. A urethane material comprising the reaction product of an A-side and a B-side;
   wherein the A-side comprises at least one isocyanate component; and
   wherein the B-side comprises an oxidized vegetable oil polyol with an acid value of from about 1.0 mg KOH/gram polyol to about 3.0 KOH/gram polyol and having a hydroxyl value of greater than about 56 mg KOH/gram formed by reacting a vegetable oil with an oxidizing compound in the presence of a tetra amido macrocyclic ligand catalyst.

2. The urethane material of claim 1, wherein the B-side further comprises at least one or more other active hydrogen-containing compounds; a catalyst; a blowing agent; a surfactant; an adhesion promoter; a coupling agent; a mold release agent; and a molecular sieve.

3. The urethane material of claim 2, wherein the at least one or more other active hydrogen containing compound is chosen from the group consisting of a multi-functional alcohol, a cross-linking agent, and a chain extender; wherein the multifunctional alcohol is at least one multifunctional alcohol chosen from the group consisting of glycerin, sucrose, and mixtures thereof; wherein the crosslinking agent is a triol or higher functional polyol; and wherein the chain extender is a chain extender chosen from the group consisting of 1,4-butanediol, dialkyl substituted methylene dianiline, diethyltoluene diamine, substituted toluene diamines, ethylene glycol, propylene glycol, diethylene glycol, dipropylene glycol, and mixtures thereof.

4. The urethane material of claim 2, wherein the catalyst comprises a catalyst chosen from the group consisting of tertiary amines; dimethylethanolamine; triphenylphosphine; mono-, di- and tri- aliphatic and alkanol amines; pyridines; piperidines; aromatic amines; ammonia; ureas; quinolines; imidazoles; imidazolines; heterocyclic nitrogen compounds; organometallic catalysts; metal carbonyls; phosphine or phosphite complexes; dialkyl tin salts of carboxylic acids; and mixtures thereof; the blowing agent comprises a blowing agent chosen from the group consisting of air, water, a methyl isobutyl ketone, acetone, methylene chloride, an aliphatic hydrocarbon, a hydroflurocarbon, a hydrochloroflurocarbon, and mixtures thereof; the surfactant comprises a silicone surfactant; the adhesion promoter comprises an adhesion promoter chosen from the group consisting of amino alkoxy silanes, vinyl alkoxy silanes, and mixtures thereof; the mold release agent comprises an organophosphate ester; and the molecular sieve comprises a zeolite.

5. The urethane material of claim 1, wherein the A-side consists of a methylenebisdiphenyl diisocyanate.

6. The urethane material of claim 1, wherein the B-side further comprises a petroleum-derived polyol wherein the petroleum derived polyol is a petroleum derived polyol chosen from the group consisting of a propylene oxide adduct of glycerol, a polyether polyol, a polyester polyol, or mixtures thereof; and the B-side further comprises a castor oil.

7. The urethane material of claim 1, wherein the B-side further comprises a castor oil.

8. The urethane material of claim 1, wherein the B-side comprises at least two oxidized vegetable oil polyols with an acid value of from about 1.0 mg KOH/gram polyol to about 3.0 mg KOH/gram polyol.

9. The urethane material of 1, wherein the B-side further comprises a blown vegetable oil that is not the at least one oxidized vegetable oil polyol wherein the blown vegetable oil, when blown, has an increased hydroxyl functionality as compared to the same vegetable oil that has not been blown.

10. A urethane material comprising the reaction product of an A-side comprising a compound having isocyanate functional groups and a B-side comprising at least one soybean oil-derived polyol having an acid value of from about 1.0 mg KOH/gram polyol to about 3.0 mg KOH/gram polyol; a petroleum-derived polyol; a castor oil; a chain extender; a cross-linking agent; a mold release compound; a molecular sieve; and an organometallic catalyst.

11. The urethane material of claim 10, wherein the compound having isocyanate functional groups comprises a methylenebisdiphenyl diisocyanate, the organometallic catalyst comprises an organometallic oxidation catalyst, and the B-side comprises:
- about 26% by weight of a combination of two soybean oil-derived polyols;
- about 35% by weight polyether polyol;
- about 23% by weight castor oil;
- about 5% by weight chain extender;
- about 5% by weight cross-linking agent;
- about 3% by weight mold release compound;
- about 2% by weight molecular sieve; and
- about 0.4% by weight organometallic oxidation catalyst.

12. The urethane material of claim 10, wherein at least one soybean oil derived polyol is a blown soybean oil polyol with a reduced acid value of from about 1.0 KOH/gram polyol to about 3.0 KOH/gram polyol and wherein the B-side comprises:
- about 26% by weight blown soybean oil polyol;
- about 35% by weight propoxylated glycerol;
- about 23% by weight castor oil;
- about 5% by weight 1, 4-butanediol;
- about 5% by weight glycerin;
- about 3% by weight organophosphate ester;
- about 2% by weight zeolite; and
- about 0.4% by weight organometallic oxidation catalyst.

13. A urethane material comprising the reaction product of an A-side comprising a compound having isocyanate functional groups and a B-side comprising a first polyol component chosen from the group consisting of at least one soybean oil-derived polyol having an acid value of from about 1.0 mg KOH/gram polyol to about 3.0 mg KOH/gram polyol; a second polyol component consisting of at least one petroleum-derived polyol; a third polyol component consisting of castor oil; a fourth polyol component consisting of multifunctional alcohol; a molecular sieve; and an organometallic catalyst.

14. The urethane material of claim 13, wherein the compound having isocyanate functional groups comprises methylenebisdiphenyl diisocyanate and the organometallic catalyst comprises an organometallic oxidation catalyst and the B-side comprises:
- about 25% by weight of the first polyol component;
- about 35% by weight of the second polyol component and the second polyol component is a polyether polyol;
- about 26% by weight of the third polyol component;
- about 10% by weight of the fourth polyol component and the multifunctional alcohol is a cross-linking agent;
- about 2% by weight molecular sieve; and
- about 0.6% by weight organometallic oxidation catalyst.

15. The urethane material of claim 13, wherein the first polyol component is a blown soybean oil polyol with a reduced acid value of from about 1.0 KOH/gram polyol to about 3.0 mg KOH/gram polyol and wherein the B-side comprises:
- about 25% by weight of the first polyol component;
- about 35% by weight of the second polyol component and the second polyol component is a propoxylated glycerol;
- about 26% by weight of the third polyol component;
- about 10% by weight of the fourth polyol component and wherein the fourth polyol component is glycerin;
- about 2% by weight zeolite; and
- about 0.6% by weight organometallic oxidation catalyst.

16. The urethane material of claim 13, wherein the compound having isocyanate functional groups comprises methylenebisdiphenyl diisocyanate, the organometallic catalyst comprises an organometallic oxidation catalyst, and the B-side comprises:
- about 26% by weight of the first polyol component wherein the first polyol component is a single soybean oil-derived polyol;
- about 25% by weight of the second polyol component and the second polyol component is a polyether polyol;
- about 26% by weight of the third polyol component;
- about 5% by weight of the fourth polyol component and wherein the fourth polyol component is a cross-linking agent;
- about 2% by weight molecular sieve; and
- about 0.6% by weight organometallic oxidation catalyst.

* * * * *